US008811695B2

(12) United States Patent
Dekel

(10) Patent No.: US 8,811,695 B2
(45) Date of Patent: Aug. 19, 2014

(54) METHODS, APPARATUS AND ARTICLES OF MANUFACTURE TO ADAPTIVELY RECONSTRUCT MEDICAL DIAGNOSTIC IMAGES

(75) Inventor: Shai Dekel, Ramat-Hasharon (IL)

(73) Assignee: General Electric Company, Schenectady, NY (US)

( * ) Notice: Subject to any disclaimer, the term of this patent is extended or adjusted under 35 U.S.C. 154(b) by 443 days.

(21) Appl. No.: 12/967,935

(22) Filed: Dec. 14, 2010

(65) Prior Publication Data

US 2012/0148125 A1 Jun. 14, 2012

(51) Int. Cl.
*G06K 9/00* (2006.01)

(52) U.S. Cl.
USPC .................... 382/128; 382/131; 378/4; 378/5

(58) Field of Classification Search
USPC .................................. 382/128, 131; 378/4, 5
See application file for complete search history.

(56) References Cited

U.S. PATENT DOCUMENTS

| | | | | |
|---|---|---|---|---|
| 6,765,983 | B2 * | 7/2004 | Yan et al. | 378/8 |
| 7,796,835 | B2 * | 9/2010 | Matsumoto | 382/276 |
| 2004/0167806 | A1 * | 8/2004 | Eichhorn et al. | 705/3 |
| 2006/0188137 | A1 * | 8/2006 | Bacus et al. | 382/128 |
| 2007/0206719 | A1 * | 9/2007 | Suryanarayanan et al. | 378/4 |
| 2008/0240533 | A1 * | 10/2008 | Piron et al. | 382/131 |
| 2008/0260092 | A1 * | 10/2008 | Imai et al. | 378/5 |
| 2009/0208086 | A1 | 8/2009 | Pelc | |
| 2009/0274355 | A1 * | 11/2009 | Chen et al. | 382/131 |
| 2009/0290768 | A1 * | 11/2009 | De La Torre-Bueno | 382/128 |
| 2010/0135453 | A1 | 6/2010 | Mendonca et al. | |
| 2010/0166274 | A1 | 7/2010 | Busch et al. | |
| 2010/0266181 | A1 * | 10/2010 | Oeckl et al. | 382/131 |
| 2011/0105880 | A1 * | 5/2011 | Yu et al. | 600/407 |
| 2011/0142316 | A1 * | 6/2011 | Wang et al. | 382/131 |

OTHER PUBLICATIONS

Barnes, Eric, "MBIR aims to outshine ASIR for sharpness, CT dose reduction," AuntMinnie.com, May 18, 2010. (6 pages).
Clunie, David A., "New Modality Issues: DICOM Enhanced Images CT, MR, PET, XA/XRF," RadPharm, Inc., Dec. 2006. (127 pages).
Panknin et al., "CT moves ahead with multiple energy sources," Diagnostic Imaging Europe, Feb. 1, 2009. (7 pages).
Freiherr, George, "Iterative reconstruction techniques cut CT dose," Diagnostic Imaging, May 22, 2009. (2 pages).
Yu et al., "Fast Model-Based X-ray CT Reconstruction Using Spatially Non-Homogeneous ICD Optimization," IEEE Transactions on Image Processing, vol. 20, No. 1, pp. 161-175, Jan. 2011. (32 pages).
Yu et al. "Non-homogeneous ICD Optimization for Targeted Reconstruction of Volumetric CT," Proc. of SPIE-IS&T Electronic Imaging, SPIE-IS&T/ vol. 6814, 2008. (8 pages).
Johnson et al. "Material differentiation by dual energy CT: initial experience," European Radiology (2007) 17: 1510-1517, 2007. (8 pages).

* cited by examiner

*Primary Examiner* — Matthew Bella
*Assistant Examiner* — Julian Brooks
(74) *Attorney, Agent, or Firm* — Hanley, Flight & Zimmerman, LLC

(57) ABSTRACT

Example methods, apparatus and articles of manufacture to adaptively reconstruct medical diagnostic images are disclosed. A disclosed example method includes storing non-reconstructed image data captured by a medical image acquisition system, receiving a parameter representing a region of interest from a diagnostic imaging workstation, and communicating a portion of the non-reconstructed image data associated with the region of interest to the diagnostic imaging workstation in response to receiving the parameter, wherein the portion of the non-reconstructed image data is processed by the diagnostic imaging workstation to form a medical diagnostic image.

19 Claims, 7 Drawing Sheets

IMAGE SERVER
WORKSTATION REQUEST LOWER QUALITY IMAGE(S)
705
YES
NO
RETURN LOW QUALITY IMAGE(S) TO WORKSTATION
710
WORKSTATION REQUEST HIGHER QUALITY IMAGE(S)
715
NO
YES
OBTAIN RAW DATA FOR ROI
720
RETURN RAW DATA FOR ROI TO WORKSTATION
725

METHODS, APPARATUS AND ARTICLES OF MANUFACTURE TO ADAPTIVELY RECONSTRUCT MEDICAL DIAGNOSTIC IMAGES

FIELD OF THE DISCLOSURE

This disclosure relates generally to medical diagnostic images and, more particularly, to methods, apparatus and articles of manufacture to adaptively reconstruct medical diagnostic images.

BACKGROUND

A widely used medical diagnostic technique includes the reconstruction of medical diagnostic images to assist in the diagnosis of medical conditions. For example, computed tomography (CT) reconstruction involves the generation a three-dimensional image of an object from a series of two-dimensional x-ray images taken around a single axis of rotation.

BRIEF DESCRIPTION OF THE INVENTION

Example methods, apparatus and articles of manufacture to adaptively reconstruct medical diagnostic images are disclosed. A disclosed example method includes storing non-reconstructed image data captured by a medical image acquisition system, receiving a parameter representing a region of interest from a diagnostic imaging workstation, and communicating a portion of the non-reconstructed image data associated with the region of interest to the diagnostic imaging workstation in response to receiving the parameter, wherein the portion of the non-reconstructed image data is processed by the diagnostic imaging workstation to form a medical diagnostic image.

A disclosed example apparatus includes an image database to store non-reconstructed image data captured by a medical image acquisition system, and an image server to receive a parameter representing a region of interest from a diagnostic imaging workstation, and communicate a portion of the non-reconstructed image data associated with the region of interest to the diagnostic imaging workstation in response to receiving the parameter, wherein the portion of the non-reconstructed image data is processed by the diagnostic imaging workstation to form a medical diagnostic image.

A disclosed example computer-readable storage medium stores machine-readable instructions that, when executed, cause a machine to at least store non-reconstructed image data captured by a medical image acquisition system, receive a parameter representing a region of interest from a diagnostic imaging workstation, reconstruct a portion of the non-reconstructed image data associated with the region of interest to form a medical diagnostic image in response to the parameter, and communicate the medical diagnostic image to the diagnostic imaging workstation.

Another disclosed example method includes presenting one or more first medical images, receiving a region of interest selection corresponding to a portion of the one or more first medical images, communicating the region of interest selection to a diagnostic image server, receiving non-reconstructed image data corresponding to the region of interest selection, forming one or more second medical images from the non-reconstructed image data, wherein the one or more second medical images are higher quality than the one or more first medical images, and presenting the one or more second medical images.

Another disclosed example apparatus includes a display device to present one or more first medical images, an input device to receive a region of interest selection corresponding to a portion of the one or more first medical images, and an image server interface to communicate the region of interest selection to a diagnostic image server, and receive one or more second medical images from the diagnostic image server, wherein the one or more second medical images correspond to the region of interest and are higher quality than the one or more first medical images, wherein the display device is to present the one or more second medical images.

DETAILED DESCRIPTION

In the interest of brevity and clarity, throughout the following disclosure references will be made to example diagnostic imaging workstations 105 and 106 and an example diagnostic imaging server 110. However, the methods, apparatus and articles of manufacture disclosed herein to adaptive reconstruct medical diagnostic images may be implemented by and/or within any number and/or type(s) of additional and/or alternative diagnostic imaging systems. For example, the methods, apparatus and articles of manufacture disclosed herein could be implemented by or within a device and/or system that captures medical diagnostic images (e.g., a computed-tomography (CT) system, a magnetic resonance imaging (MRI) system, an X-ray imaging system, and/or an ultrasound imaging system), and/or by or within a system and/or workstation designed for use in viewing, analyzing, storing and/or archiving medical diagnostic images (e.g., the GE® picture archiving and communication system (PACS), and/or the GE advanced workstation (AW)). Further, the example methods, apparatus and articles of manufacture disclosed herein may be used to adaptively reconstruct one-dimensional (1D), two-dimensional (2D), three-dimensional (3D), and/or four-dimensional (4D) images or datasets.

Figure 1:
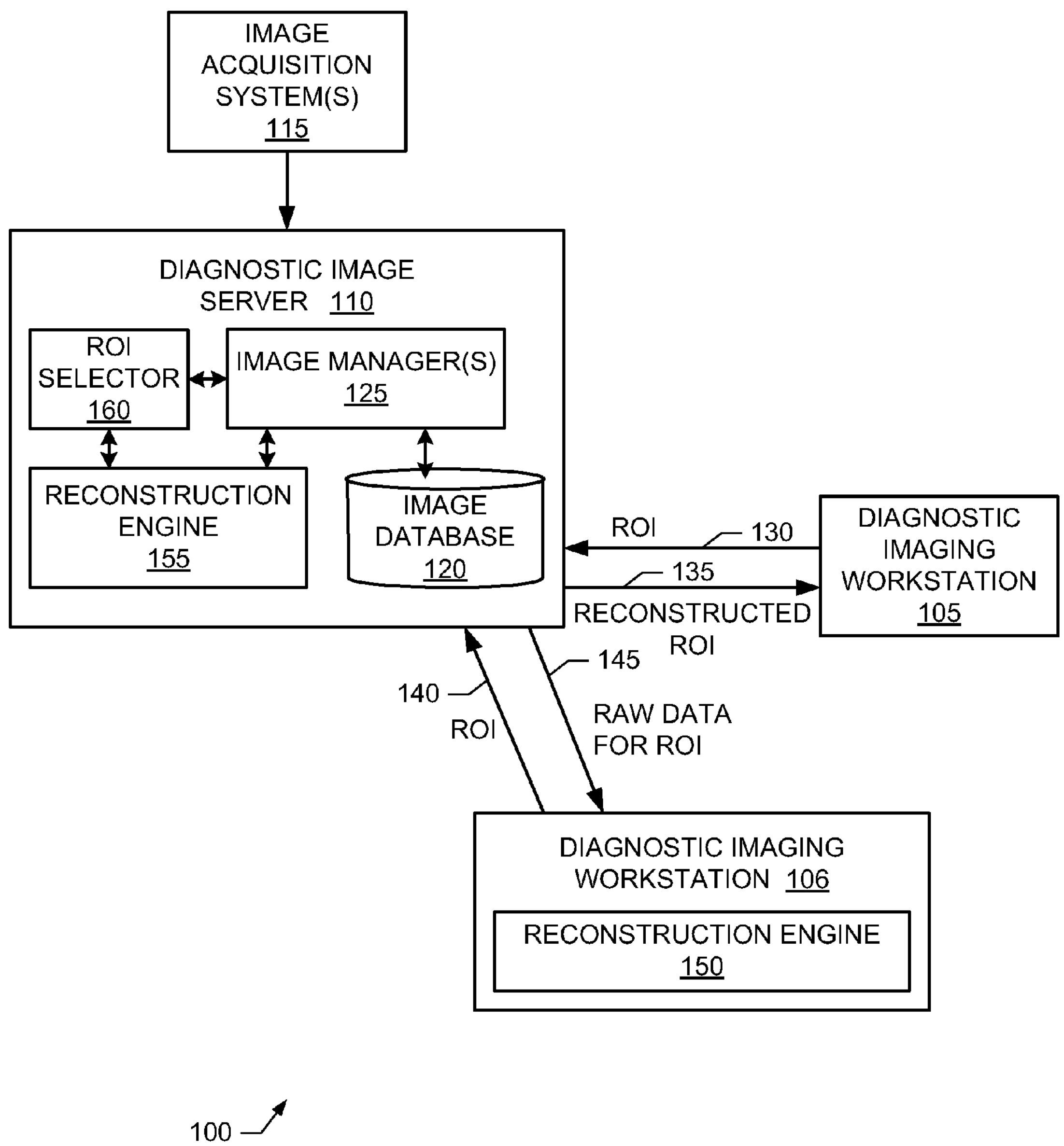
FIG. 1 is a schematic illustration of an example diagnostic imaging system implemented in accordance with the teachings of this disclosure.

FIG. 1 illustrates an example diagnostic imaging system 100 that adaptively reconstructs diagnostic medical images based on user selected region of interests (ROIs). The example diagnostic imaging system 100 includes the example diagnostic imaging workstations 105 and 106 and the example diagnostic image server 110. The medical diagnostic images may be captured by any number and/or type(s) of image acquisition system(s) 115, and stored in any number and/or type(s) of image database(s) 120 managed and/or controlled by any number and/or type(s) of image manager(s) 120. Example image acquisition systems 115 include, but are not limited to, an X-ray imaging system, an Ultrasound imaging system, a CT imaging system and/or an MRI system.

Traditionally, medical diagnostic image reconstruction (e.g., computed tomography (CT) reconstruction) is performed by the image acquisition system(s) 115 and the reconstructed images are subsequently provided to the diagnostic image server 110 for storage, retrieval and/or archiving. While advancement in medical diagnostic image reconstruction have significantly improved image quality and/or diagnostic accuracy, some emerging reconstruction techniques and/or methods may take one or more hours to perform a high-fidelity and/or higher-quality reconstruction. Accordingly, image reconstruction may become a bottle-neck in radiology departments and may, in some instances, introduce an unfortunate delay in obtaining diagnostic information in urgent and/or emergent care environments.

Additionally, a user (e.g., a doctor, a radiologist, a technician, etc.) may only need, require and/or desire the high-fidelity reconstructed images for one, a few and/or small clinical regions of interest (ROIs). However, current diagnostic imaging systems are not able to determine and/or identify a priori the areas of clinical interest.

Further, during spectral CT, patients are usually scanned using a dual energy mode at tube voltages of 140 and 80 peak kilovoltage (kVp). The dual energy mode enables subsequent image processing to better distinguish different materials. For example, calcium (bone) and iodine (present in a contrast agent) have similar attenuation coefficients at around energy 80 kilo-electronvolt (keV), but have different attenuations at other energies. Thus, acquiring two CT scans at different energies enables a better differentiation of materials. Additionally, emerging spectral CT techniques differentiate materials without the injection of contrast agents and/or using contrast agents specifically designed for dual energy acquisition.

Traditionally, once dual energy CT image data is acquired, both sets of data are reconstructed and stored separately as two sets of reconstructed image data. Alternatively, a "projection-based" material representation reconstruction may be performed, from which other material decompositions can be computed. However, the mathematics of CT reconstruction and, specifically, the handing of the noise are such that one can compute higher quality images from the raw data (i.e., the originally captured image data) for each energy. Thus, there is a benefit to store the raw data and perform adaptive reconstruction adaptively as a user (e.g., a doctor, a radiologist, a technician, etc.) identifies clinical ROIs. For example, from a dual energy acquisition, a virtual scan at another energy level can be computed. The computation of this virtual scan at a third energy level is more accurate when the raw data of the two acquired energies is available.

To overcome at least these deficiencies, the example diagnostic imaging system 100 of FIG. 1 stores the diagnostic image data captured by the example image acquisition system (s) 115 as original and/or raw image data. In other words, the original and/or raw image data is stored without a need to perform any reconstruction prior to storing the original and/or raw image data in the image database 120. Because the original and/or raw image data is stored without having to perform a reconstruction on the image data, the original and/or raw image data is also referred to herein as non-reconstructed image data. However, while the example image database 120 of FIG. 1 stores the original, raw and/or non-reconstructed image data, the example image database 120 may additionally store reconstructed images corresponding to the non-reconstructed image data. For example, the image acquisition system(s) 115 may perform an image reconstruction to generate low-quality and/or low-fidelity corresponding images. Additionally or alternatively, the example diagnostic image server 110 may perform the image reconstruction to generate additional and/or alternative low-quality and/or low-fidelity images. The diagnostic image server 110 may generate the low-quality and/or low-fidelity images when the corresponding non-reconstructed image data is stored in the image database 120 and/or on-the-fly when a user (e.g., a doctor, a radiologist, a technician, etc.) desires to view the diagnostic images. Any or all of these low-quality and/or low-fidelity images are suitable and/or sufficient to allow a user using one of the example diagnostic imaging workstations 105, 106 to browse the low-quality and/or low-fidelity images and/or to identify clinical ROIs. Moreover, the low-quality and/or low-fidelity images may be readily communicated across low-bandwidth communication paths, to remote location and/or to mobile medical diagnostic equipment.

Non-reconstructed image data and/or diagnostic images may be stored in the example image database 120 using any number and/or type(s) of data structure(s). For example, image data and/or images may be stored in the image database 120 in accordance with any past, present and/or future digital imaging and communication in medicine (DICOM) standard. The example image database 120 may be implemented by any number and/or type(s) of volatile and/or non-volatile memory (-ies), memory device(s) and/or storage device(s) such as a hard disk drive, a compact disc (CD), a digital versatile disc (DVD), etc.

In some examples, as a user (e.g., a doctor, a radiologist, a technician, etc.) begins by navigating a set of lower-quality and/or lower-fidelity images (e.g., computed using a first-generation CT reconstruction technique). When, for example, the user zooms in on a clinical ROI (e.g., a particular CT slice), the example diagnostic imaging system 100 performs local higher-quality and/or higher-fidelity reconstruction for the selected ROI. In an example, a user reviews CT slices in so-called Axial or 2D mode, that is, the user is browsing (stacking) through the reconstructed lower-quality and/or lower-fidelity CT slices. When the user focuses on a particular slice, the computation of a higher-quality and/or higher-fidelity reconstruction of that slice is performed and/or initiated. For the purpose of reconstructing the selected CT slice, only the original, raw and/or non-reconstructed CT image data corresponding to the 'region' around the slice is used. In some examples, an iterative reconstruction technique applies more reconstruction updates to the pixels of the selected slice; fewer reconstruction updates to adjacent and/or nearby slices; and completely ignores other slices. Additionally or alternatively, the selected slice is progressively reconstructed, with quality increasing as more iterations are applied in the background.

When a user (e.g., a doctor, a radiologist, a technician, etc.) using the example diagnostic imaging workstation 106 of FIG. 1 identifies and/or selects one or more ROIs, the diagnostic imaging workstation 106 communicates the selected ROIs 130 to the diagnostic image server 110. In response, the example image manager 125 of FIG. 1 provides the original, raw and/or non-reconstructed image data 135 corresponding to the identified ROIs to the diagnostic imaging workstation 106. A reconstruction engine 150 implemented at and/or by the diagnostic imaging workstation 106 performs a second, higher-quality and/or higher-fidelity reconstruction for the selected ROI(s) from the received original, raw and/or non-reconstructed image data 135. The higher-quality and/or higher-fidelity images are presented at the diagnostic imaging workstation 106 to the user. Thus, the second, higher-quality and/or higher-fidelity reconstruction is only performed for the selected ROI(s) 130 and only as and/or when user selects the ROI(s). In other words, the higher-quality and/or higher-fidelity reconstruction is performed and/or carried out adaptively in response to use of the diagnostic imaging workstation 106 by the user.

In some examples involving spectral CT, the higher-quality and/or higher-fidelity reconstruction may depend on the type and/or features of materials (e.g., calcium, iodine, etc.) that the user wants to analyze. Further, the higher-quality and/or higher-fidelity reconstruction may depend on the selected energy level for a simulated virtual scan. Additionally and/or alternatively, reconstruction parameters may be adjusted to accommodate lower sampling rates and/or data transmission rates.

Additionally or alternatively, when a user (e.g., a doctor, a radiologist, a technician, etc.) using the example diagnostic imaging workstation 105 of FIG. 1 identifies and/or selects one or more ROIs, the diagnostic imaging workstation 105 communicates the selected ROIs 140 to the example diagnostic image server 110. In response, a reconstruction engine 155 implemented at and/or by the example diagnostic image server 110 of FIG. 1 performs a second, higher-quality and/or higher-fidelity reconstruction for the original, raw and/or non-reconstructed image data corresponding to the selected ROI(s). The example image manager 125 provides the higher-quality and/or higher-fidelity reconstructed images 145 to the diagnostic imaging workstation 105. The higher-quality and/or higher-fidelity images 145 are presented at the diagnostic imaging workstation 106 to the user. Thus, the second, higher-quality and/or higher-fidelity reconstruction is only performed for the selected ROI(s) 140 and only as and/or when the user selects the ROI(s). In other words, the higher-quality and/or higher-fidelity reconstruction is performed and/or carried out adaptively in response to use of the diagnostic imaging workstation 105 by the user.

To perform image reconstruction, the example diagnostic image server 110 and the example diagnostic imaging workstation 106 include the example reconstruction engine(s) 150 and 155. The example reconstruction engine(s) 150 and 155 of FIG. 1 are configured, implemented and/or programmed to implement any number and/or type(s) of reconstruction technique(s), method(s) and/or algorithm(s). The example reconstruction engines 150 and 155 of FIG. 1 may implement the same and/or different reconstruction techniques, methods and/or algorithms. Example reconstruction techniques that may be implemented by the example reconstruction engines 150 and 155 include, but are not limited to, filtered backprojection, adaptive statistical iterative reconstruction, and/or model-based image reconstruction. Example methods and apparatus to perform filtered backprojection are described by Jiang Hseigh in a book entitled "Computed Tomography ($2^{nd}$ Edition)" and published in 2009 by Wiley-Interscience, which is hereby incorporated by reference in its entirety. Example methods and apparatus to perform adaptive statistical iterative reconstruction are described in by Jiang Hseigh in a book entitled "Computed Tomography ($2^{nd}$ Edition) and published in 2009 by Wiley-Interscience, and in a paper by Gary Freiherr entitled "Iterative Reconstruction Techniques Cut CT Dose" and published in 2009 at DiagnosticImaging.com, which is hereby incorporated by reference in its entirety. Example methods and apparatus to perform model-based image reconstruction are described in an article entitled "MBIR Aims to Outshine ASIR For Sharpness, CT Dose Reduction" published in AuntMinnie in 2010, and in an paper by Yu et al. entitled "Fast Model-Based X-ray CT Reconstruction Using Spatially Non-Homogeneous ICD Optimization," which is to appear in Transactions on Image Processing. The AuntMinnie and Yu et al. papers are hereby incorporated by reference in their entireties.

To identify potential diagnostic ROIs, the example diagnostic image server 110 may optionally include a ROI identifier 160. Using any number and/or type(s) of method(s), technique(s), algorithm(s) and/or logic, the example ROI identifier 160 of FIG. 1 processes the images received from the image acquisition system(s) 115 to identify ROIs that may be of potential interest to medical personnel (e.g., a doctor, a technician, a radiologist, etc.). For ROIs or larger regions including potential ROIs identified by the example ROI selector 160, the example reconstruction engine 155 may pre-compute higher-quality and/or higher-fidelity reconstructions prior to selection of those ROIs by a user (e.g., a doctor, a radiologist, a technician, etc.) of the example diagnostic imaging workstations 105 and 106. Such pre-computation of higher-quality and/or higher-fidelity reconstructions may be performed in addition to and/or as an alternative to the adaptive reconstruction of images disclosed herein.

Moreover, in some examples, the diagnostic image server 110 computes higher-quality and/or higher-fidelity reconstructed images without first identifying potential ROIs or receiving a user selected ROI. For example, in addition to placing the original, raw and/or non-reconstructed image data in the image database 120, the original, raw and/or non-reconstructed image data may also be placed in a processing queue. When the image acquisition system 115 provides corresponding lower-quality and/or lower-fidelity images, the lower-fidelity and/or lower-quality images may be replaced, over time, by corresponding higher-quality and/or higher-fidelity images computed by the reconstruction engine 155. When the image acquisition system 115 does not provide corresponding lower-quality and/or lower-fidelity images, the reconstruction engine 155 may compute lower-quality and/or lower-fidelity images and then, over time, replace those lower-quality and/or lower-fidelity images with corresponding higher-quality and/or higher-fidelity images. As images of lower and/or higher quality or fidelity are computed, the images are stored in the image database 120 together with an indicator of quality level. Were a user (e.g., a doctor, a radiologist, a technician, etc.) to begin interacting with the example diagnostic imaging system 100 prior to completion of the processing of the original, raw and/or non-reconstructed image data, the example image manager(s) 125 can determine whether the ROI(s) selected by the user already have corresponding reconstructed images (of lower and/or higher quality or fidelity) and which ROIs need to be adaptively reconstructed, as disclosed herein.

While the example diagnostic imaging system 100 is illustrated in FIG. 1, one or more of the elements, processes and/or devices illustrated in FIG. 1 may be combined, divided, re-arranged, omitted, eliminated and/or implemented in any other way. For example, the diagnostic image server 110 may not implement the example reconstruction engine 155 and/or both of the example diagnostic imaging workstations 105 and 106 may implement the reconstruction engine 150. Further, the example diagnostic imaging workstations 105 and 106, the example diagnostic image server 110, the example image acquisition system(s) 115, the example image database 120, the example image manager(s) 125, the example reconstruction engines 150 and 155 and/or the example ROI selector 160 may be implemented by hardware, software, firmware and/or any combination of hardware, software and/or firmware. Thus, for example, any of the diagnostic imaging workstations 105 and 106, the example diagnostic image server 110, the example image acquisition system(s) 115, the example image database 120, the example image manager(s) 125, the example reconstruction engines 150 and 155 and/or, the example ROI selector 160 could be implemented by the example processor platform P100 of FIG. 10 and/or one or more circuit(s), programmable processor(s), application specific integrated circuit(s) (ASIC(s)), programmable logic device(s) (PLD(s)) and/or field programmable logic device(s) (FPLD(s)), field-programmable gate array(s) (FPGA(s)), fuses, etc. When any apparatus claim of this patent incorporating one or more of these elements is read to cover a purely software and/or firmware implementation, at least one of the example diagnostic imaging workstations 105 and 106, the example diagnostic image server 110, the example image acquisition system(s) 115, the example image database 120, the example image manager(s) 125, the example reconstruction engines 150 and 155 and/or the example ROI selector 160 are hereby expressly defined to include a tangible article of manufacture such as a tangible computer-readable medium storing the firmware and/or software. Further still, the example diagnostic imaging system 100 may include one or more elements, processes and/or devices in addition to, or instead of, those illustrated in FIG. 1, and/or may include more than one of any or all of the illustrated elements, processes and devices.

As used herein, the term tangible computer-readable medium is expressly defined to include any type of computer-readable medium and to expressly exclude propagating signals. Example computer-readable medium include, but are not limited to, a volatile or non-volatile memory, a volatile or non-volatile memory device, a CD, a DVD, a floppy disk, a read-only memory (ROM), a random-access memory (RAM), a programmable ROM (PROM), an electronically-programmable ROM (EPROM), an electronically-erasable PROM (EEPROM), an optical storage disk, an optical storage device, magnetic storage disk, a magnetic storage device, a cache, and/or any other storage media in which information is stored for any duration (e.g., for extended time periods, permanently, brief instances, for temporarily buffering, and/or for caching of the information) and which can be accessed by a processor, a computer and/or other machine having a processor, such as the example processor platform P100 discussed below in connection with FIG. 10. As used herein, the term non-transitory computer-readable medium is expressly defined to include any type of computer-readable medium and to exclude propagating signals.

Figure 2:
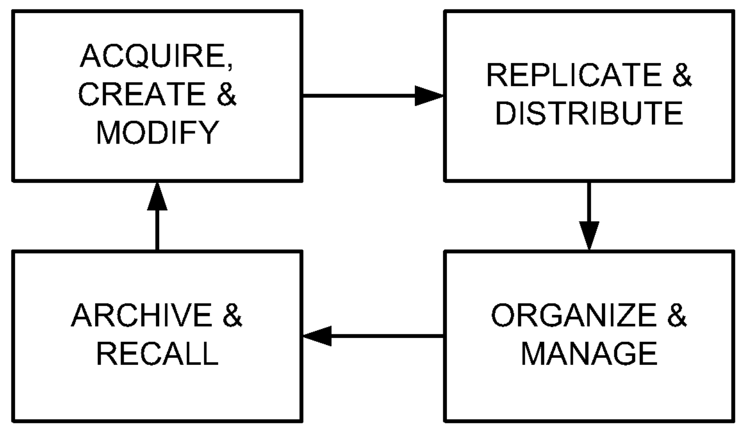
FIG. 2 illustrates an example image lifecycle management flow within which the example methods, apparatus and articles of manufacture disclosed herein may be implemented.

FIG. 2 illustrates an example image lifecycle management flow 200 that may be implemented by the example diagnostic imaging system 100 of FIG. 1. Medical diagnostic image data is acquired, created and/or modified by the image acquisition system(s) 115. The image manager(s) 125 replicate, distribute, organize and/or otherwise manage the captured images. The example diagnostic imaging workstations 105 and 106 of FIG. 1, among other things, enable users (e.g., a doctor, a radiologist, a technician, etc.) to adaptively select and view higher-quality and/or higher-quality reconstructed images.

Figure 3:
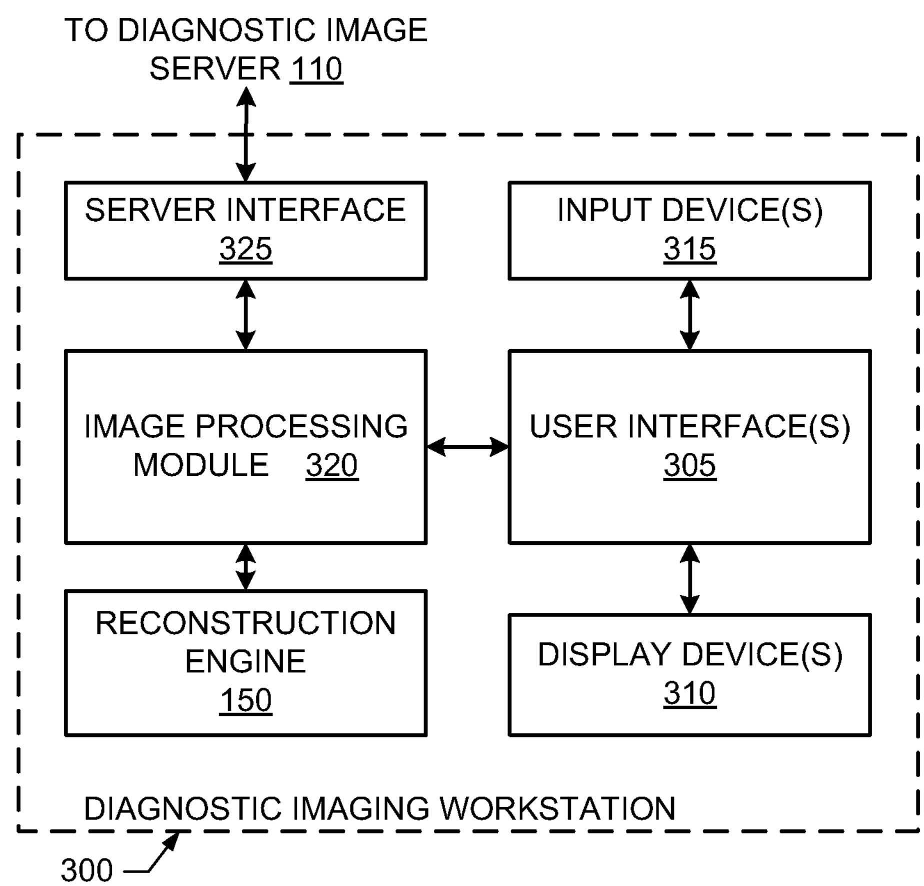
FIG. 3 is an example block diagram that can be used to implement the examples disclosed herein.

FIG. 3 illustrates an example manner of implementing the example diagnostic imaging workstations 105 and 106 of FIG. 1. While the example workstation depicted in FIG. 3 may be used to implement either or both of the diagnostic imaging workstations 105 and 106, for ease of discussion the example diagnostic imaging workstation of FIG. 3 will be referred to as diagnostic imaging workstation 300.

To allow a user (not shown) to interact with the example diagnostic imaging workstation 105 of FIG. 3, the diagnostic imaging workstation 300 of FIG. 3 includes any number and/or type(s) of user interface module(s) 305, any number and/or type(s) of display device(s) 310 and any number and/or type(s) of input device(s) 315. The example user interface module(s) 305 of FIG. 3 implements an operating system to present user interfaces presenting information (e.g., images, segmentations, account information, patient information, windows, screens, interfaces, dialog boxes, etc.) at the display device(s) 310, and to allow a user to control, configure and/or operate the example diagnostic imaging workstation 300. The user provides and/or makes inputs and/or selections to the user interface module 305 and/or, more generally, to the example diagnostic imaging workstation 300 via the input device(s) 315. Example input devices 315 include, but are not limited to, a keyboard, a touch screen and/or a mouse.

In an example, a patient search window is presented at the display device 310, and the input device(s) 315 are used to enter search criteria to identify a particular patient. When a patient is identified and selected, the example user interface 305 presents a list of available medical diagnostic images for the patient at the display device 310, and the user selects one or more imaging studies using the input device(s) 315. An image processing module 320 obtains low-quality and/or lower-fidelity image(s) for the selected imaging study(-ies) from the example diagnostic image server 110 via a server interface 325. The image-processing module 320 presents the image(s) and implements a user interface to allow a user to browse the image(s) and/or to select one or more clinical ROIs. When a ROI is selected, the image processing module 320 communicates the selected ROIs to the example diagnostic image server 110 via the server interface 325.

In response, the example diagnostic image server 110 of FIG. 1 provides either original, raw and/or non-reconstructed image data and/or corresponding higher-quality and/or higher-fidelity diagnostic images to the diagnostic imaging workstation 300. When higher-quality and/or higher-fidelity diagnostic images are received, the image processing module 320 presents the higher-quality and/or higher-fidelity diagnostic images via the user interface 305. When non-reconstructed image data is received, the example reconstruction engine 150 performs a higher-quality and/or higher-fidelity reconstruction for the non-reconstructed image data, and the image processing module 320 presents the resulting higher-quality and/or higher-fidelity diagnostic images via the user interface 305.

While an example manner of implementing the example diagnostic imaging workstations 105 and 106 of FIG. 1 have been illustrated in FIG. 3, one or more of the elements, processes and/or devices illustrated in FIG. 3 may be combined, divided, re-arranged, omitted, eliminated and/or implemented in any other way. For example, the diagnostic imaging workstation 300 may not implement the example reconstruction engine 150. Further, the example user interface(s) 305, the example display device(s) 310, the example input device(s) 315, the example image processing module 320, the example server interface 325, the example reconstruction engine 150 and/or the example diagnostic imaging workstation 300 of FIG. 3 may be implemented by hardware, software, firmware and/or any combination of hardware, software and/or firmware. Thus, for example, any of the example user interface(s) 305, the example display device(s) 310, the example input device(s) 315, the example image processing module 320, the example server interface 325, the example reconstruction engine 150 and/or the example diagnostic imaging workstation 300 could be implemented by the example processor platform P100 of FIG. 10 and/or one or more circuit(s), programmable processor(s), ASIC(s), PLD(s) and/or FPLD(s), FPGA(s), fuses, etc. When any apparatus claim of this patent incorporating one or more of these elements is read to cover a purely software and/or firmware implementation, at least one of the example user interface(s) 305, the example display device(s) 310, the example input device(s) 315, the example image processing module 320, the example server interface 325, the example reconstruction engine 150 and/or the example diagnostic imaging workstation 300 are hereby expressly defined to include a tangible article of manufacture such as a tangible computer-readable medium storing the firmware and/or software. Further still, the example diagnostic imaging workstation 300 may include one or more elements, processes and/or devices in addition to, or instead of, those illustrated in FIG. 1, and/or may include more than one of any or all of the illustrated elements, processes and devices.

Figure 4:
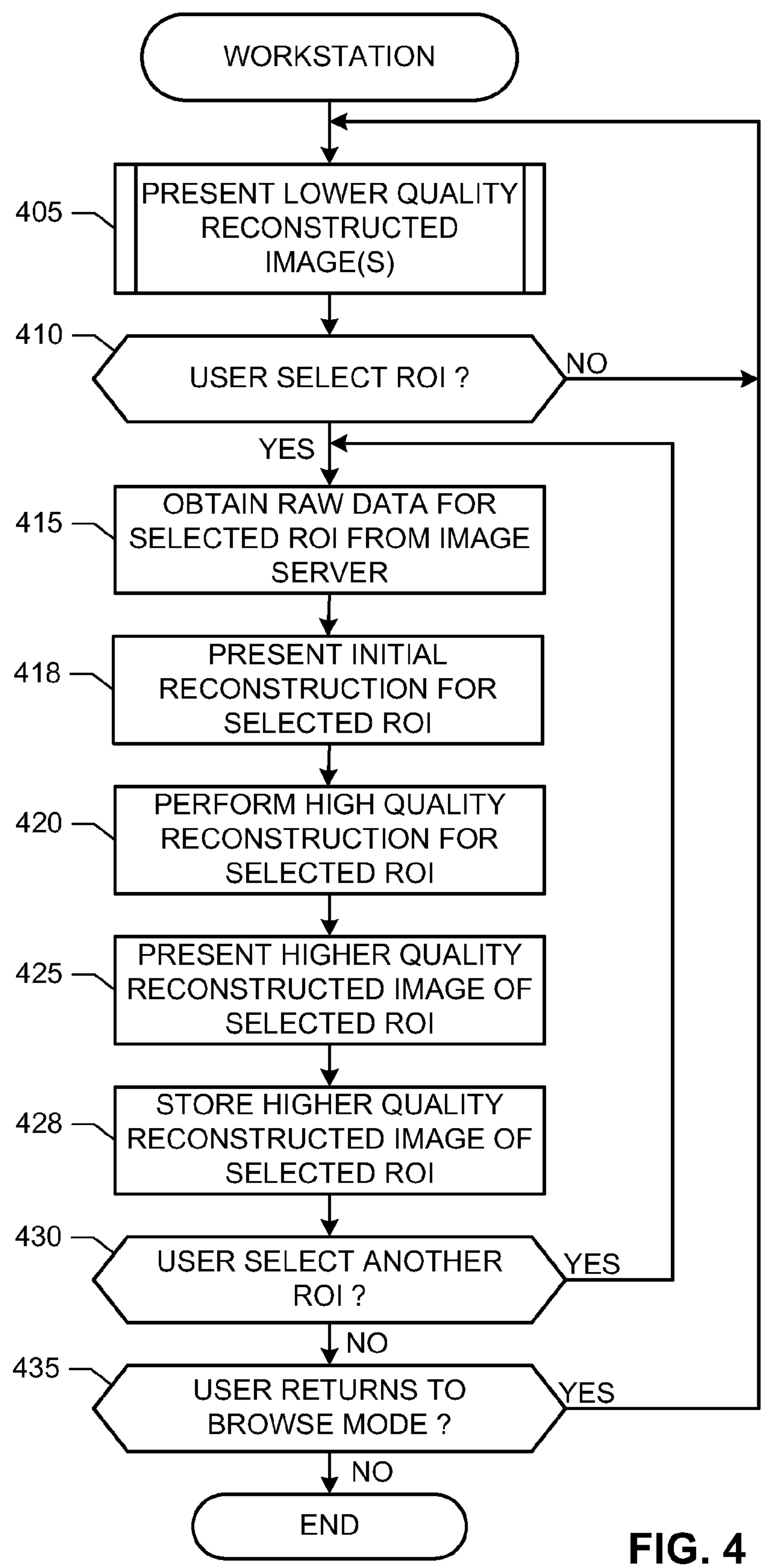
FIGS. 4 and 5 are flowcharts representative of example processes that may be embodied as machine-accessible instructions and executed by, for example, one or more processors to implement the example diagnostic workstations of FIGS. 1 and 2.
Figure 5:
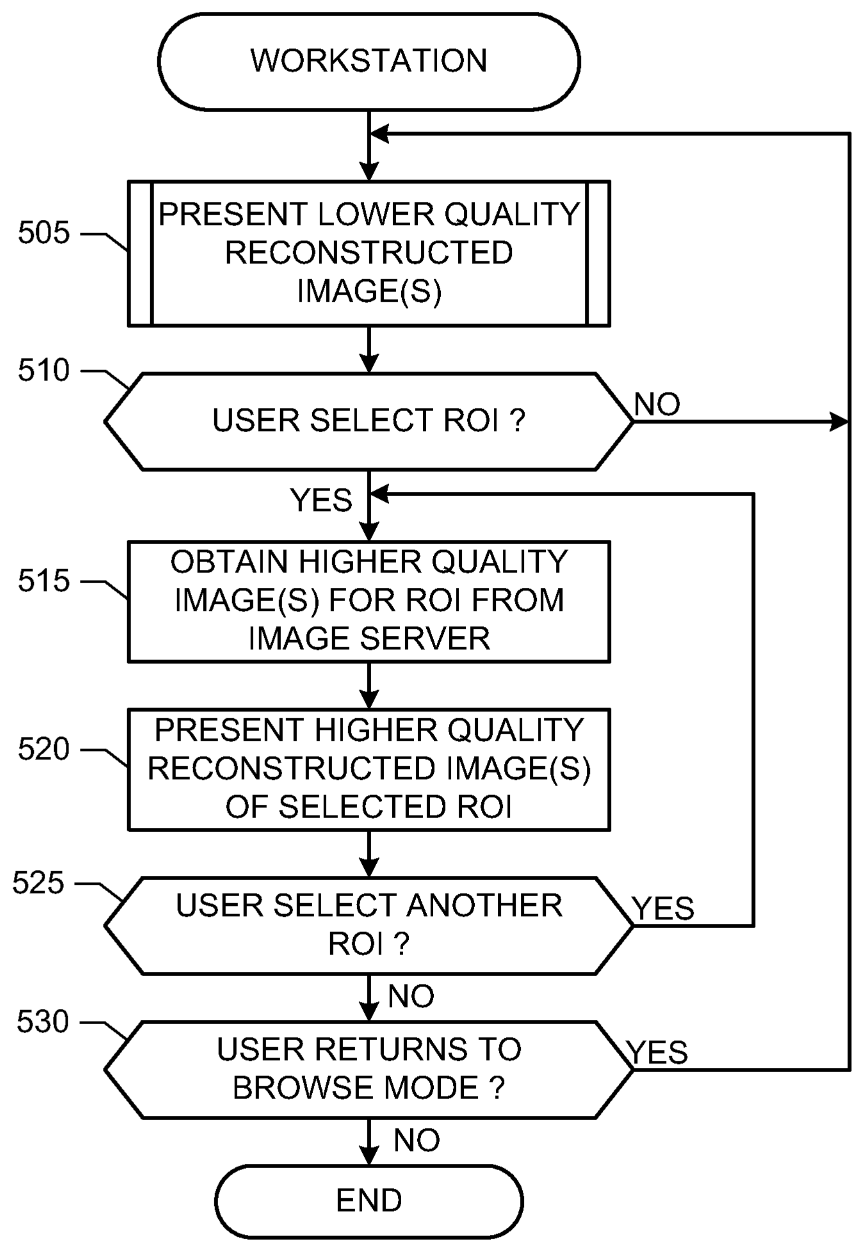
Figure 6:
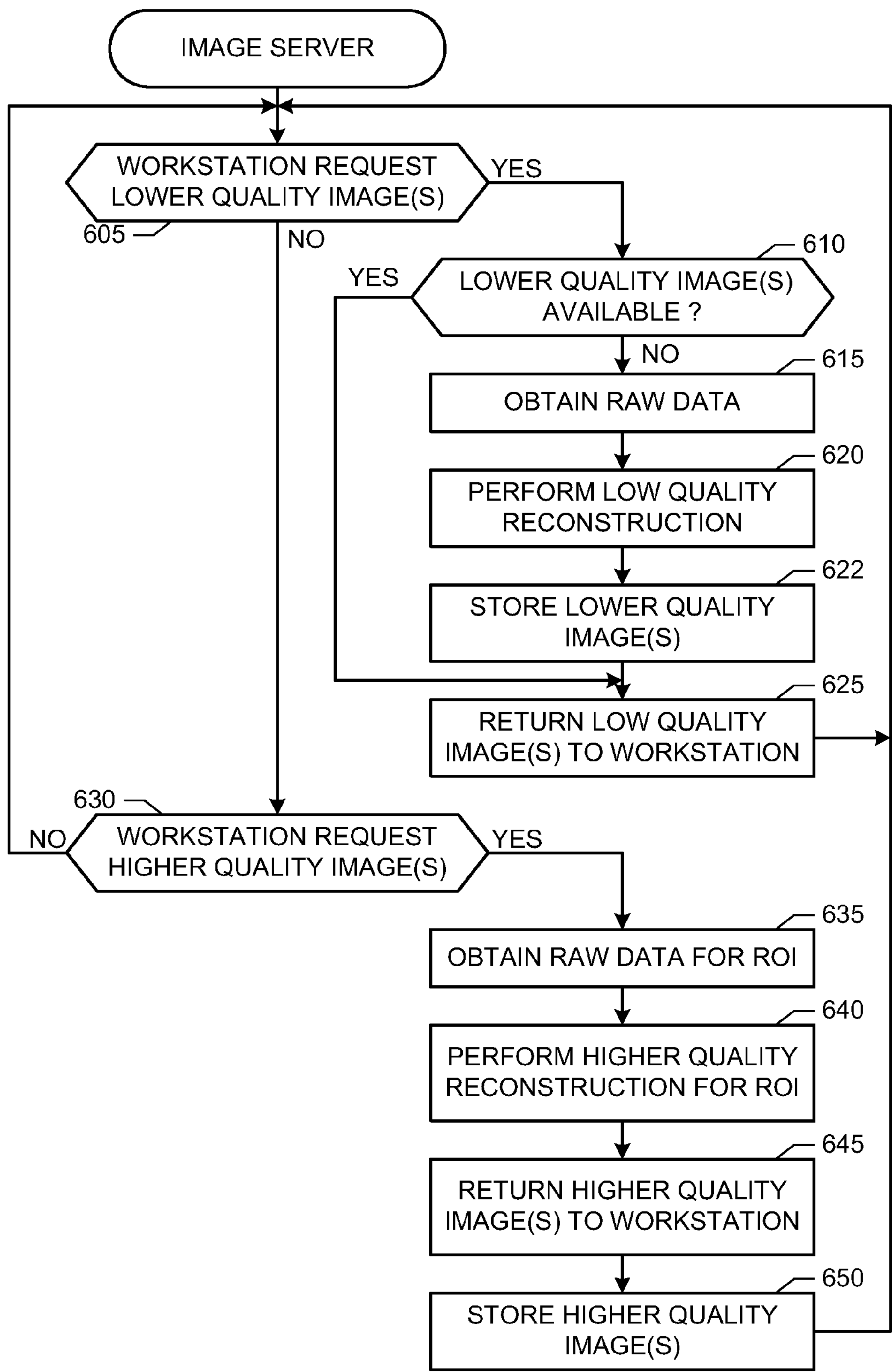
FIGS. 6 and 7 are flowcharts representative of example processes that may be embodied as machine-accessible instructions and executed by, for example, one or more processors to implement the example diagnostic image server of FIG. 1.
Figure 7:
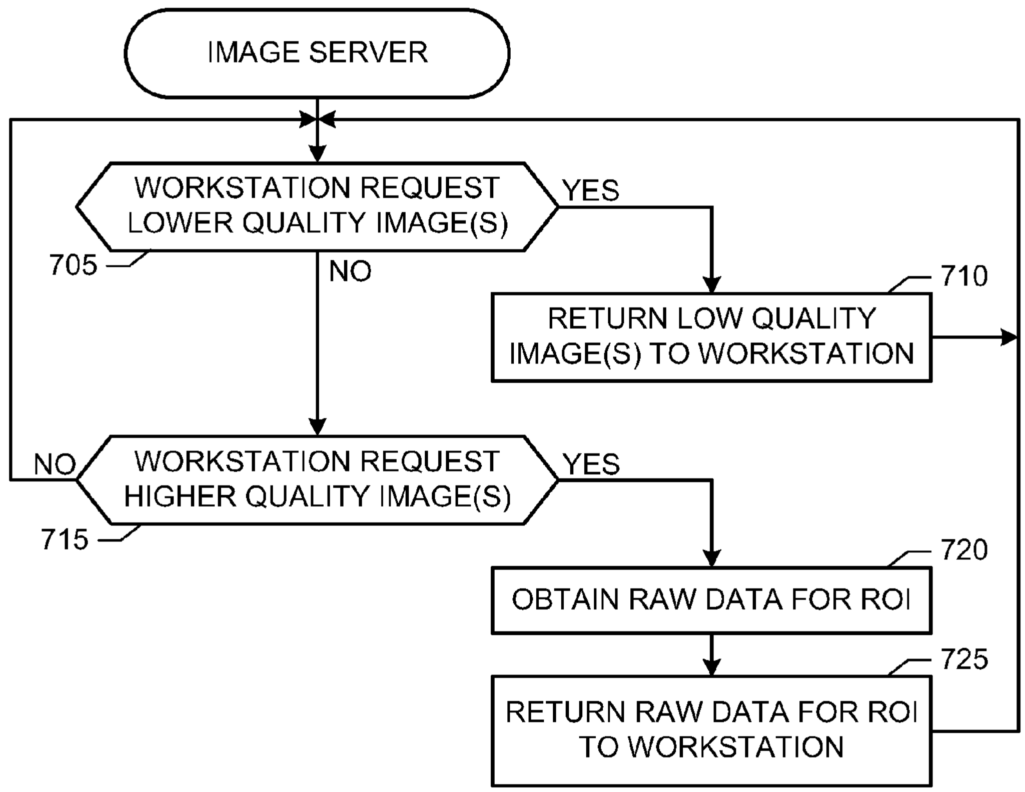

FIGS. 4 and 5 are flowcharts representing example processes that may be embodied as machine-accessible instructions and executed by, for example, one or more processors to implement the example diagnostic imaging workstations 105, 106 and 300 of FIGS. 1 and 3. FIGS. 6 and 7 are flowcharts representing example processes that may be embodied as machine-accessible instructions and executed by, for example, one or more processors to implement the example diagnostic image server 110 of FIG. 1. A processor, a controller and/or any other suitable processing device may be used, configured and/or programmed to execute the example machine-readable instructions represented in FIGS. 4-7. For example, the processes of FIGS. 4-7 may be embodied in coded instructions stored on a tangible computer-readable medium. Machine-readable instructions comprise, for example, instructions that cause a processor, a computer and/or a machine having a processor to perform one or more particular processes. Alternatively, some or all of the example processes of FIGS. 4-7 may be implemented using any combination(s) of ASIC(s), PLD(s), FPLD(s), FPGA(s), discrete logic, hardware, firmware, etc. Also, some or all of the example processes of FIGS. 4-7 may be implemented manually or as any combination of any of the foregoing techniques, for example, any combination of firmware, software, discrete logic and/or hardware. Further, many other methods of implementing the example operations of FIGS. 4-7 may be employed. For example, the order of execution of the blocks may be changed, and/or one or more of the blocks described may be changed, eliminated, sub-divided, or combined. Additionally, the blocks of the example processes of FIGS. 4-7 may be carried out sequentially and/or carried out in parallel by, for example, separate processing threads, processors, devices, discrete logic, circuits, etc.

The example process of FIG. 4 begins with the example image processing module 320 present one or more lower-quality reconstructed images via the example user interface 305 (block 405). When a user (e.g., a doctor, a radiologist, a technician, etc.) selects and/or identifies a ROI (block 410), the image processing module 320 obtains raw, original and/or non-reconstructed image data for the ROI from the diagnostic image server 110 (block 415). The example reconstruction engine 150 performs, if needed, an initial and/or lower-fidelity reconstruction for the non-reconstructed image data and the image processing module 320 presents the resulting image(s) (block 418). Additionally or alternatively, the image processing module 320 may obtain the initial and/or lower-fidelity reconstruction image(s) from the diagnostic image server 110. The example reconstruction engine 150 performs a higher-quality and/or higher-fidelity reconstruction for the non-reconstructed image data (block 420) and the image processing module 320 presents the resulting higher-quality and/or higher-fidelity images via the user interface 305 (block 425). The workstation 106 stores the resulting higher-quality and/or higher-fidelity images at the diagnostic image server 110 for subsequent retrieval (block 428).

If the user selects another ROI (block 430), control returns to block 415 to obtain additional non-reconstructed image data.

If the user does not select another ROI (block 430), but selects to return to browse mode using the initial low-quality and/or lower-fidelity images (block 430), control returns to block 405. Otherwise, control exits from the example process of FIG. 4.

Compared to FIG. 4, in the example process of FIG. 5, the example diagnostic image server 110 performs the higher-quality and/or higher-fidelity reconstruction. The example process of FIG. 5 begins with the example image processing module 320 presenting one or more lower-quality reconstructed images via the example user interface 305 (block 505). When a user (e.g., a radiologist and/or technician) selects and/or identifies a ROI (block 510), the image processing module 320 obtains higher-quality and/or higher-fidelity reconstructed images corresponding to the selected ROI from the diagnostic image server 110 (block 515). The image processing module 320 presents the resulting higher-quality and/or higher-fidelity images via the user interface 305 (block 520).

If the user selects another ROI (block 525), control returns to block 515 to obtain additional higher-quality and/or higher-fidelity reconstructed images.

If the user does not select another ROI (block 525), but selects to return to browse mode using the initial low-quality and/or lower-fidelity images (block 530), control returns to block 505. Otherwise, control exits from the example process of FIG. 5.

The example process of FIG. 6 begins with the image manager 125 determining whether a request for low-quality and/or lower-fidelity reconstructed images was received (block 605). When a request for low-quality and/or lower-fidelity reconstructed images is received (block 605), the image manager 125 queries the image database 120 to determine whether low-quality and/or lower-fidelity reconstructed images are available (block 610). If low-quality and/or lower-fidelity reconstructed images are not available (block 610), the image manager 125 obtains corresponding original, raw and/or non-reconstructed image data (block 615) and the example reconstruction engine 155 performs a low-quality and/or lower-fidelity reconstruction (block 620). The image manager 125 stores the resulting low-quality and/or lower-fidelity images in the image database 120 for subsequent retrieval (block 622). The image manager 125 communicates the low-quality and/or lower-fidelity images to the diagnostic imaging workstation (block 625). Control then returns to block 605.

Returning to block 610, if low-quality and/or lower-fidelity reconstructed images are available (block 610), the image manager 125 communicates the low-quality and/or lower-fidelity images to the diagnostic imaging workstation (block 625) and control returns to block 605.

Returning to block 605, if a request for low-quality and/or lower-fidelity reconstructed images was not received (block 605), the image manager 125 determines whether a request for higher-quality and/or higher-fidelity images corresponding to a selected ROI was received (block 635). When a request for higher-quality and/or higher-fidelity images corresponding to a selected ROI is received (block 635), the image manager 125 obtains the original, raw and/or non-reconstructed image data corresponding to the selected ROI (block 635) and the example reconstruction engine 155 performs a higher-quality and/or higher-fidelity reconstruction (block 640). The image manager 125 communicates the higher-quality and/or higher-fidelity images to the diagnostic imaging workstation (block 645). The image manager 125 stores the resulting higher-quality and/or higher-fidelity images in the image database 120 for subsequent retrieval (block 650). Control then returns to block 605.

Compared to the example of FIG. 6, in the example process of FIG. 7, the diagnostic image server 110 does not implement the example reconstruction engine 155. The example process of FIG. 7 begins when the image manager 125 determining whether a request for low-quality and/or lower-fidelity reconstructed images was received (block 705). When a request for low-quality and/or lower-fidelity reconstructed images is received (block 705), the image manager 125 communicates the low-quality and/or lower-fidelity images to the diagnostic imaging workstation (block 710) and control returns to block 705.

Returning to block 705, if a request for low-quality and/or lower-fidelity reconstructed images was not received (block 705), the image manager 125 determines whether a request for higher-quality and/or higher-fidelity images corresponding to a selected ROI was received (block 715). When a request for higher-quality and/or higher-fidelity images corresponding to a selected ROI is received (block 715), the image manager 125 obtains the original, raw and/or non-reconstructed image data corresponding to the selected ROI (block 720) and communicates the original, raw and/or non-reconstructed image data corresponding to the selected ROI to the diagnostic imaging workstation (block 725). Control then returns to block 705.

Figure 8:
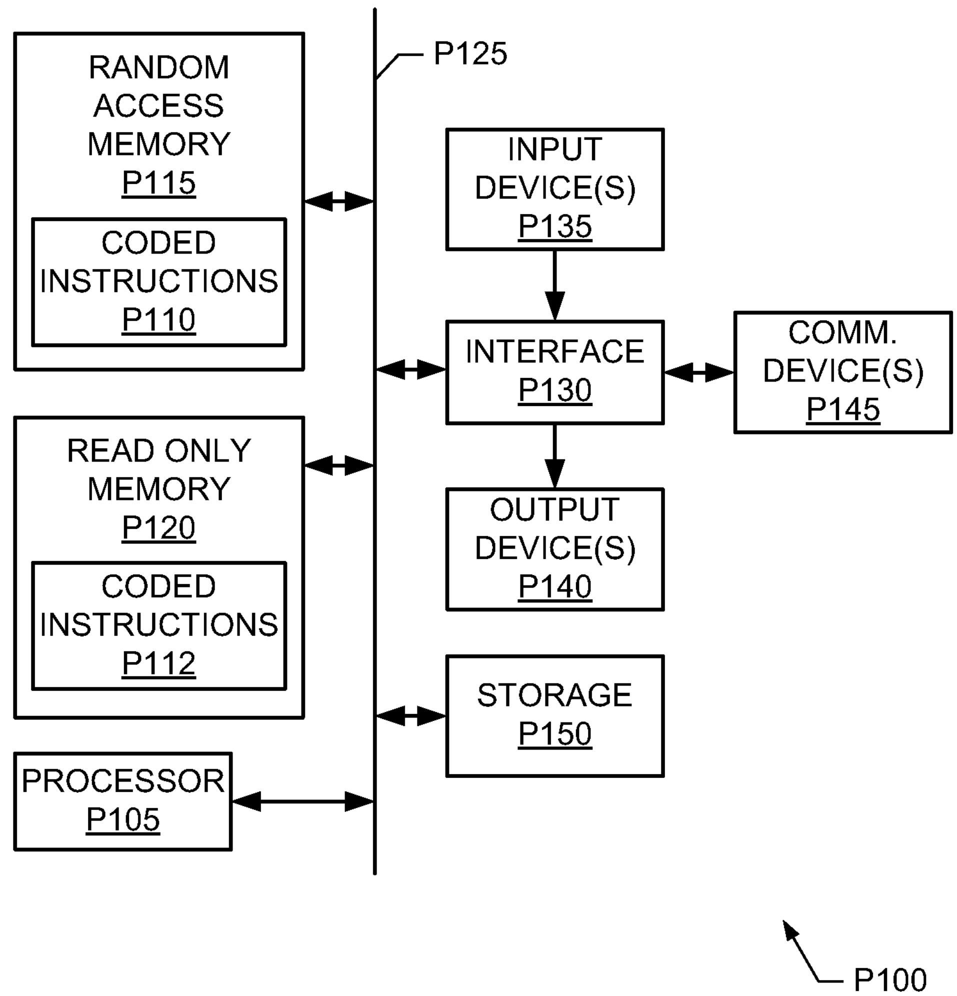
FIG. 8 is a schematic illustration of an example processor platform that may be used and/or programmed to carry out the example processes of FIGS. 4-7 to implement the example methods, apparatus and articles of manufacture disclosed herein.

FIG. 8 is a block diagram of an example processor platform P100 capable of executing the example instructions of FIGS. 4-7 to implement the example diagnostic image server 110 and/or the example diagnostic image workstations 105, 106 and 300 of FIGS. 1 and 3. The example processor platform P100 can be, for example, a PC, a workstation, a laptop, a server and/or any other type of computing device containing a processor.

The processor platform P100 of the instant example includes at least one programmable processor P105. For example, the processor P105 can be implemented by one or more Intel® microprocessors from the Pentium® family, the Itanium® family or the XScale® family. Of course, other processors from other processor families and/or manufacturers are also appropriate. The processor P105 executes coded instructions P110 and/or P112 present in main memory of the processor P105 (e.g., within a volatile memory P115 and/or a non-volatile memory P120) and/or in a storage device P150. The processor P105 may execute, among other things, the example machine-accessible instructions of FIGS. 4-7 to adaptively reconstructed medical diagnostic images. Thus, the coded instructions P110, P112 may include the example instructions of FIGS. 4-7.

The processor P105 is in communication with the main memory including the non-volatile memory P110 and the volatile memory P115, and the storage device P150 via a bus P125. The volatile memory P115 may be implemented by Synchronous Dynamic Random Access Memory (SDRAM), Dynamic Random Access Memory (DRAM), RAMBUS Dynamic Random Access Memory (RDRAM) and/or any other type of RAM device. The non-volatile memory P110 may be implemented by flash memory and/or any other desired type of memory device. Access to the memory P115 and the memory P120 may be controlled by a memory controller.

The processor platform P100 also includes an interface circuit P130. Any type of interface standard, such as an external memory interface, serial port, general-purpose input/output, as an Ethernet interface, a universal serial bus (USB), and/or a PCI express interface, etc, may implement the interface circuit P130.

The interface circuit P130 may also includes one or more communication device(s) 145 such as a network interface card to communicatively couple the processor platform P100 to, for example, the example imaging manager 110 and/or the example diagnostic imaging workstations 105, 106 and 300 of FIGS. 1 and 3.

In some examples, the processor platform P100 also includes one or more mass storage devices P150 to store software and/or data. Examples of such storage devices P150 include a floppy disk drive, a hard disk drive, a solid-state hard disk drive, a CD drive, a DVD drive and/or any other solid-state, magnetic and/or optical storage device. The example storage devices P150 may be used to, for example, store the example coded instructions of FIGS. 4-7 and/or the example image database 120 of FIG. 1.

Generally, computer-executable instructions include routines, programs, objects, components, data structures, etc., that perform particular tasks or implement particular abstract data types. Computer-executable instructions, associated data structures, and program modules represent examples of program code for executing the processes to implement the example methods and systems disclosed herein. The particular sequence of such executable instructions and/or associated data structures represent examples of corresponding acts for implementing the examples disclosed herein.

The example methods, apparatus and articles of manufacture disclosed herein may be practiced in a networked environment using logical connections to one or more remote computers having processors. Example logical connections include, but are not limited to, a local area network (LAN) and a wide area network (WAN). Such networking environments are commonplace in office-wide or enterprise-wide computer networks, intranets and the Internet and may use a wide variety of different communication protocols. Such network computing environments may encompass many types of computer system configurations, including personal computers, hand-held devices, multi-processor systems, microprocessor-based or programmable consumer electronics, network PCs, minicomputers, mainframe computers, and the like. The example methods, apparatus and articles of manufacture disclosed herein may, additionally or alternatively, be practiced in distributed computing environments where tasks are performed by local and remote processing devices that are linked (either by hardwired links, wireless links, or by a combination of hardwired or wireless links) through a communications network. In a distributed computing environment, program modules may be located in both local and remote memory storage devices.

Although certain example methods, apparatus and articles of manufacture have been disclosed herein, the scope of coverage of this patent is not limited thereto. On the contrary, this patent covers all methods, apparatus and articles of manufacture fairly falling within the scope of the appended claims either literally or under the doctrine of equivalents.

What is claimed is:

1. A method comprising:

storing, at a diagnostic image server, non-reconstructed image data captured by a medical image acquisition system;

communicating, by the diagnostic image server, first medical diagnostic images to a first diagnostic imaging workstation, the first medical diagnostic images reconstructed from the non-reconstructed image data;

receiving, by the diagnostic image server, a parameter representing a region of interest from the first diagnostic imaging workstation, the region of interest selected from the first medical diagnostic images; and communicating, by the diagnostic image server, only a portion of the non-reconstructed image data associated with the region of interest to the first diagnostic imaging workstation in response to receiving the parameter, wherein the portion of the non-reconstructed image data is to be processed by the first diagnostic imaging workstation to form a second medical diagnostic image of higher quality than the first medical diagnostic images.

2. A method as defined in claim 1, further comprising:

receiving first medical diagnostic images reconstructed from the non-reconstructed image data by the medical image acquisition system; and storing the first medical diagnostic images.

3. A method as defined in claim 1, further comprising:

receiving a second parameter representing a second region of interest from a second diagnostic imaging workstation;

reconstructing a second portion of the non-reconstructed image data associated with the second region of interest to form a third medical diagnostic image; and communicating the third medical diagnostic image to the second diagnostic imaging workstation.

4. A method as defined in claim 1, wherein the medical image acquisition system comprises at least one of a computed tomography system or a magnetic resonance imaging system.

5. A method as defined in claim 1, wherein:

the non-reconstructed image data comprises a first set of non-reconstructed image data captured at a first energy, and a second set of non-reconstructed image data captured at a second energy; and the processing by the first diagnostic imaging workstation comprises processing a portion of the first and second sets of non-reconstructed image data to perform a virtual scan at a third energy.

6. An apparatus comprising:

an image database to store non-reconstructed image data captured by a medical image acquisition system; and an image server to receive a parameter representing a region of interest from a first diagnostic imaging workstation, the region of interest selected from first medical diagnostic images reconstructed from the non-reconstructed image data, and communicate only a portion of the non-reconstructed image data associated with the region of interest to the first diagnostic imaging workstation in response to receiving the parameter, wherein the portion of the non-reconstructed image data is to be processed by the first diagnostic imaging workstation to form a second medical diagnostic image of higher quality than the first medical diagnostic images.

7. An apparatus as defined in claim 6, further comprising a reconstruction engine to reconstruct the non-reconstructed image data to form the first medical diagnostic images, wherein the image database is to store the first medical diagnostic images.

8. An apparatus as defined in claim 7, wherein the image server is to communicate the first medical diagnostic images to the first diagnostic imaging workstation, the first medical diagnostic images to be presented at the first diagnostic imaging workstation to facilitate selection of the region of interest.

9. An apparatus as defined in claim 6, wherein the image server is to receive a second parameter representing a second region of interest from a second diagnostic imaging workstation, and further comprising a reconstruction engine to reconstruct a second portion of the non-reconstructed image data associated with the second region of interest to form a third medical diagnostic image, wherein the image server is to communicate the third medical diagnostic image to the second diagnostic imaging workstation.

10. An apparatus as defined in claim 6, wherein the medical image acquisition system comprises at least one of a computed tomography system or a magnetic resonance imaging system.

11. An apparatus as defined in claim 6, wherein:

the non-reconstructed image data comprises a first set of non-reconstructed image data captured at a first energy, and a second set of non-reconstructed image data captured at a second energy; and the first diagnostic imaging workstation is to process a portion of the first and second sets of non-reconstructed image data to perform a virtual scan at a third energy.

12. An article of manufacture comprising a tangible computer-readable storage medium storing machine-readable instructions that, when executed, cause a machine to at least:

store, at a diagnostic image server, non-reconstructed original image data captured by a medical image acquisition system; and communicating, by the diagnostic image server, only a portion of the non-reconstructed image data associated with a region of interest to a first diagnostic imaging workstation in response to receiving a parameter representing the region of interest from the first diagnostic imaging workstation, the region of interest selected from first medical diagnostic images reconstructed from the non-reconstructed image data, wherein the portion of the non-reconstructed image data is to be processed by the first diagnostic imaging workstation to form a second medical diagnostic image of higher quality than the first medical diagnostic images.

13. An article of manufacture as defined in claim 12, wherein the machine-readable instructions, when executed, cause the machine to:

in response to receiving, a second parameter representing a second region of interest from a second diagnostic imaging workstation, communicating a second portion of the non-reconstructed image data associated with the second region of interest to the second diagnostic imaging workstation, wherein the second portion of the non-reconstructed image data is to be processed by the second diagnostic imaging workstation to form a third medical diagnostic image.

14. An article of manufacture as defined in claim 12, wherein the machine-readable instructions, when executed, cause the machine to:

reconstruct the non-reconstructed image data to form first medical diagnostic images; and store the first medical diagnostic images.

15. An article of manufacture as defined in claim 14, wherein the machine-readable instructions, when executed, cause the machine to communicate the first medical diagnostic images to the first diagnostic imaging workstation, the first medical diagnostic images to be presented at the first diagnostic imaging workstation to facilitate selection of the region of interest.

16. An article of manufacture as defined in claim 12, wherein the machine-readable instructions, when executed, cause the machine to:

in response to receiving first medical diagnostic images reconstructed from the non-reconstructed image data by the medical image acquisition system, store the first medical diagnostic images.

17. An article of manufacture as defined in claim 16, wherein the machine-readable instructions, when executed, cause the machine to communicate the first medical diagnostic images to the first diagnostic imaging workstation, the first medical diagnostic images presented at the first diagnostic imaging workstation to facilitate selection of the region of interest.

18. An article of manufacture as defined in claim 12, wherein the medical image acquisition system comprises at least one of a computed tomography system or a magnetic resonance imaging system.

19. An article of manufacture as defined in claim 12, wherein:

the non-reconstructed image data comprises a first set of non-reconstructed image data captured at a first energy, and a second set of non-reconstructed image data captured at a second energy; and the non-reconstructed image data is reconstructed by processing a portion of the first and second sets of non-reconstructed image data to perform a virtual scan at a third energy.

* * * * *

UNITED STATES PATENT AND TRADEMARK OFFICE

CERTIFICATE OF CORRECTION

PATENT NO. : 8,811,695 B2
APPLICATION NO. : 12/967935
DATED : August 19, 2014
INVENTOR(S) : Dekel It is certified that error appears in the above-identified patent and that said Letters Patent is hereby corrected as shown below:

In the Claims

Column 14, line 34, Claim 11: Delete "original" before "image"

Signed and Sealed this
Twenty-third Day of December, 2014

Michelle K. Lee

Michelle K. Lee
*Deputy Director of the United States Patent and Trademark Office*